United States Patent [19]

Warrell, Jr.

[11] Patent Number: 4,880,811
[45] Date of Patent: Nov. 14, 1989

[54] USE OF C-5 MONO-SUBSTITUTED BARBITURATES TO TREAT DISORDERS OF URIC ACID METABOLISM

[75] Inventor: Raymond P. Warrell, Jr., New York, N.Y.

[73] Assignee: Memorial Hospital for Cancer and Allied Diseases, New York, N.Y.

[21] Appl. No.: 66,616

[22] Filed: Jun. 24, 1987

[51] Int. Cl.$^4$ ............................................. A61K 31/515
[52] U.S. Cl. ..................................... 514/270; 514/825
[58] Field of Search ................. 544/299; 514/270, 825

[56] References Cited

U.S. PATENT DOCUMENTS 4,634,707  1/1987  Brewer et al. ....................... 514/270

OTHER PUBLICATIONS

The Pharmacological Basis of Therapeutics, 4th edition, D. M. Woodbury, 1970, pp. 341–347.
Arthritis and Allied Conditions, J. L. Hollander et al, 1972, pp. 1071–1111, 1112–1139.

Primary Examiner—Douglas W. Robinson
Assistant Examiner—Raymond J. Henley, III
Attorney, Agent, or Firm—John P. White

[57] ABSTRACT

The present invention provides a method for decreasing the bodily content of uric acid in a subject which comprises administrating to the subject an effective content-decreasing amount of a barbiturate compound mono-substituted at the carbon-5 position.

The invention also provides a pharmaceutical composition and a method for treating disorders of uric acid metabolism and resulting ailments in a subject.

26 Claims, No Drawings

USE OF C-5 MONO-SUBSTITUTED BARBITURATES TO TREAT DISORDERS OF URIC ACID METABOLISM

The invention described herein was made in the course of work under Grant No. N01-CM-57732 from the National Cancer Institute. The U.S. Government has certain rights in this invention.

BACKGROUND OF THE INVENTION

Throughout this application various publications are referenced and citations are provided in parentheses for them. The disclosures of these publications in their entireties are hereby incorporated by reference into this application in order to more fully describe the state of the art to which this invention pertains.

Disorders of uric acid metabolism are extremely common. These disorders may afflict 1% or more of human individuals (Hall, A. P., et al., Am. J. Med. 42: 27, 1967; Heine, J., Virchow's Arch. f. Path. Anat., 260: 521, 1926; Decker, J. L. et al., Arth. Rheum. 5: 144, 1962). The best known example is gout which causes a painful, chronic arthritis which can be extremely debilitating and can lead to extensive deformities (Wyngarden, J. B. and Kelly, W. N., *The Metabolic Basis of Inherited Disease*, 916–1010, J. B. Stanbury, J. B. Wyngarden, D. S. Fredrickson, 4th ed. McGraw-Hill: New York, 1978; Bauer, W. and Krane, S. M., *Disease of Metabolism*, 805–849, G. G. Duncan, 5th ed., Saunders: Philadelphia, 1964).

Gout may be primary or secondary. Primary gout consists of hereditary diseases which are associated with increased serum uric acid levels (hyperuricemia). Secondary gout may occur in cancers, particularly leukemias, and in other blood disorders (e.g. polycythemia, myeloid metaplasia, etc.). There exists abundant evidence that prolonged elevations of serum uric acid are associated with the deposition of sodium urate crystals in many tissues, including kidney and joints.

A variety of disorders other than gouty arthritis are associated with abnormalities of uric acid metabolism, including kidney failure and urolithiasis (urinary stones composed of uric acid) which occur in 10–18% of patients with gout and which are common sources of morbidity and mortality from the disease (Talbott, J. H. and Terplan, K. L., Medicine 39: 405, 1960; Gutman, A. B. and Yu, T. F., Am. J. Med. 23: 600, 1957). Increased uric acid has also been associated with cardiovascular disease (Kramer, D. W., et al., Angiology 9: 162, 1958), plumbism (so-called "saturnine gout" caused by exposure to lead) (Ludwig, G. D., Arch. Int. Med. 100: 802, 1957), hyperparathyroidism (Mintz, D. H., et al., New Eng. J. Med. 265: 112, 1961), psoriasis, and sarcoidosis (Kaplan, H. and Klatzkin, G., Yale J. Biol. Med. 32: 335, 1960; Bunim, J. J., et al., Ann. Int. Med. 57: 1018, 1962).

Uric acid is derived from 3 major sources (1) an end-product of the synthesis of purines without prior incorporation into nucleic acids; (2) a breakdown product of tissue nucleic acids and pre-formed coenzymes; and (3) a product of the catabolism of dietary purine-containing compounds. At the pH of body fluids, uric acid generally exists in serum as the urate ion (monosodium urate). The mean normal serum concentration of uric acid is $5.1 \pm 0.93$ mg/100 ml. The normal range for females is approximately 1 mg/100 ml below the range for males. Uric acid is excreted by glomerular filtration and tubular secretion in the kidney. A substantial fraction of the material is also reabsorbed by the renal tubules.

Several methods have been used to treat disorders of uric acid metabolism and a variety of drugs have been employed to treat the acute manifestations of painful gouty arthritis. These drugs include colchicine, aspirin, and a variety of non-steroidal anti-inflammatory compounds. These drugs are extremely effective in reducing pain due to the acute attacks of gout; however, they do not prevent recurrent attacks and they do not affect the underlying disorders of abnormal uric acid metabolism. Methods used in clinical practice which more directly treat the metabolic disorder include increasing the excretion of uric acid by the kidneys and decreasing the formation of uric acid by inhibiting steps which precede its synthesis in the body.

Probenecid is an example of a compound which has been used to increase uric acid excretion (a so-called "uricosuric" drug). Probenecid causes an increase in uric acid secretion by the renal tubules and, when used chronically, can be useful in mobilizing body stores of urate (Gutman, A. B. and Yu, T. F., Trans. Acad. Am. Phys. 64: 279, 1951). However, a substantial porportion of patients treated with probenecid fail to respond. Twenty-five to fifty percent of patients fail to achieve reduction of serum uric acid to levels less than 6 mg/100 ml. Leading causes are drug intolerance, concomitant salicylate ingestion, and renal impairment (Gutman, A. B. and Yu, T. F., Lancet ii: 1258, 1957; Thompson, G. R., et al., Arth. Rheum. 5: 384, 1962). Approximately one-third of the patients eventually develop intolerance to the drug (Wyngarden, J. B. and Kelly, W. N., supra).

An example of a drug which inhibits uric acid formation is allopurinol. Allopurinol and other pyrazolo(3,4-d)pyrimidines were first synthesized for use as cancer chemotherapeutic agents. However, the drugs proved to have little anticancer activity when used singly (Shaw, R. K., et al., Cancer 13: 482, 1960). Allopurinol is structurally very similar to hypoxanthine, differing only in the transposition of the carbon and nitrogen atoms at positions 7 and 8.

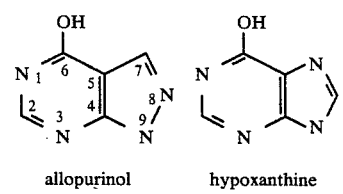

allopurinol   hypoxanthine

The compound was subsequently shown to inhibit xanthine oxidase, an enzyme which is essential for the formation of uric acid (Feigelson, P., et al., J. Biol. Chem. 226: 993, 1957). Allopurinol is itself converted to oxy-purinol wherein an alcohol is attached to the carbon-2 position. Oxy-purinol is more potent in inhibiting xanthine oxidase, but oxy-purinol is less pharmaceutically acceptable due to low oral bioavailability. The observation that patients treated for cancer with allopurinol developed a decrease in serum uric acid suggested utility as a treatment for gout (Wyngarden, J. B., et al., Arth. Rheum. 6: 306, 1963). Allopurinol has since become a standard form of therapy for hyperuricemia and uric acid stones (Rundles, R. W., et al., Ann. Int. Med. 60: 717, 1964; Wyngarden, J. B., et al., Ann. Int. Med. 62: 842, 1965; Delbarre, F., et al., Arth. Rheum. 25: 627, 1966; Rundles, R. W., et al., Ann. Int. Med. 64: 229, 1966; Woodbury, D. M., *The Pharmacological Basis of Therapeutics*, L. S. Goodman and A. Gilman, 4th ed., MacMillan: New York, 1970). Although serious toxicity is uncommon, fatal reactions due to hypersensitivity, bone marrow suppression, hepatitis, and vasculitis have been reported (Wyngarden, J. B. and Kelly, S. M., supra). The incidence of side effects may total 20% of all patients treated with the drug (id.). Treatment for disorders of uric acid metabolism has not evolved significantly in the following two decades since the introduction of allopurinol.

The present invention relates to the use of barbituric acid derivatives which have undergone mono-substitution at the carbon-5 (C-5) position for treatment of disorders of uric acid metabolism. The method of the subject invention overcomes the disadvantages and side-effects associated with the methods of the prior art, particularly the disadvantages and side-effects associated with the use of allopurinol.

It has been discovered that administration of carbon-5 monosubstituted barbiturate compounds to humans and animals unexpectedly causes a dramatic decrease in the concentration of serum uric acid. Barbiturate compounds monosubstituted at the C-5 position with groups containing less than eight (8) alkyl carbons are especially suitable for clinical treatment of disorders of uric acid metabolism since they are orally bioavailable and do not readily penetrate the central nervous system. Thus, these compounds do not share the excessively sedating properties at doses which are effective for treatment of disorders of uric acic metabolism which characterize other barbiturate compounds which have undergone di-substitution at the C-5 position (Sharpless, S. K., in L. S. Goodman and A. Gilman, supra at 98–120).

SUMMARY OF THE INVENTION

The present invention provides a method for decreasing the bodily content of uric acid in a subject which comprises administrating to the subject an effective content-decreasing amount of a compound having the structure:

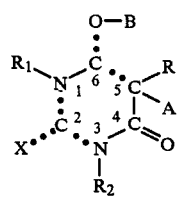

wherein:

X is an oxygen, sulfur or hydrogen atom;

R is an alkyl group, a cycloalkyl group, a phenyl group, a phenylalkyl group, a hydroxyphenyl group, a heteroatomic-substituted phenyl group, an amino group, a hydroxyl group, a heteroatomic group having two atoms to twenty atoms bound in a chain wherein each atom is independently selected from the group consisting of carbon, oxygen, sulfur and nitrogen atoms, or an aryl group comprising an aromatic ring or a cyclo group moiety bound to an alkyl group or heteroatomic group moiety having from two atoms to twenty atoms bound in a chain wherein each atom is independently selected from the group consisting of carbon, oxygen, sulfur and nitrogen atoms;

$R_1$ may be present or absent and if present is a hydrogen atom or a methyl group;

$R_2$ may be present or absent and if present is a hydrogen atom or a methyl group;

either A or B is present and the other is absent and if present is a hydrogen atom; and the dotted line ( ... ) represent bonds which may be double or single bonds;

and wherein:

the dotted line ( ... ) between C-6 and O is a double bond if A is present and a single bond if B is present;

the dotted line ( ... ) between C-6 and C-5 is a double bond if B is present and a single bond if A is present;

the dotted line ( ... ) between C-2 and X is a double bond and both $R_1$ and $R_2$ are present if X is an oxygen or sulfur atom;

the dotted line ( ... ) between C-2 and X is a single bond and either $R_1$ or $R_2$ is present and the other is absent if X is a hydrogen atom;

the dotted line ( ... ) between N-1 and C-2 is a single bond if $R_1$ is present and a double bond if $R_1$ is absent; and the dotted line ( ... ) between N-3 and C-2 is a single bond if $R_2$ is present and a double bond if $R_2$ is absent.

The invention also provides a method for treating a disorder of uric acid metabolism in a subject which comprises administrating to the subject a compound having the structure:

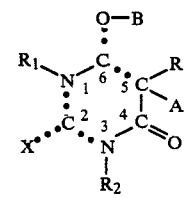

wherein X, R, $R_1$, $R_2$, A, B, and the dotted lines are the same as previously defined.

Another embodiment of the invention concerns a pharmaceutical composition for treating disorders of uric acid metabolism in a subject which comprises a pharmaceutically acceptable carrier and an effective amount of the compound defined above.

DETAILED DESCRIPTION OF THE INVENTION

The present invention provides a method for decreasing the bodily content of uric acid in a subject which comprises administrating to the subject an effective content-decreasing amount of a compound having the structure:

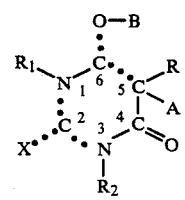

wherein:

X is an oxygen, sulfur or hydrogen atom;

R is an alkyl group, a cycloalkyl group, a phenyl group, a phenylalkyl group, a hydrophenyl group, a heteroatomic-substituted phenyl group, an amino group, a hydroxyl group, a heteroatomic group having two atoms to twenty atoms bound in a chain wherein each atom is independently selected from the group consisting of carbon, oxygen, sulfur and nitrogen atoms, or an aryl group comprising an aromatic ring or cyclo group moiety bound to an alkyl group or a heteroatomic group moiety having from two atoms to twenty atoms bound in a chain wherein each atom is independently selected from the group consisting of carbon, oxygen, sulfur and nitrogen atoms;

$R_1$ may be present or absent and if present is a hydrogen atom or a methyl group;

$R_2$ may be present or absent and if present is a hydrogen atom or a methyl group;

either A or B is present and the other is absent and if present is a hydrogen atom; and the dotted lines ( . . . ) represent bonds which may be double or single bonds; and wherein:

the dotted line ( . . . ) between C-6 and O is a double bond if A is present and a single bond if B is present;

the dotted line ( . . . ) between C-6 and C-5 is a double bond if B is present and a single bond if A is present;

the dotted line ( . . . ) between C-2 and X is a double bond and both $R_1$ and $R_2$ are present if X is an oxygen or sulfur atom;

the dotted line ( . . . ) between C-2 and X is a single bond and either $R_1$ or $R_2$ is present and the other is absent if X is a hydrogen atom;

the dotted line ( . . . ) between N-1 and C-2 is a single bond if $R_1$ is present and a double bond if $R_1$ is absent; and the dotted line ( . . . ) between N-3 and C-2 is a single bond if $R_2$ is present and a double bond if $R_2$ is absent.

In the above structure, the numerals 1-6 in the interior of the ring indicate the position of the carbon (C) and nitrogen (N) atoms forming the ring with respect to one another.

The bodily content of uric acid in a subject means the total amount of uric acid in the body of the subject, including uric acid, urate ions or sodium urate crystals in the blood serum, urine, other bodily fluids, tissues, organs or joints of the subject.

Suitable subjects for which the present invention is useful include humans and animals. Preferably, the subject has a disorder of uric acid metabolism characterized by an abnormally high bodily content of uric acid in the blood serum, urine or joints of the subject. Such disorders may include an overproduction of uric acid, a low excretion of uric acid, tumor lysis, or a blood disorder, particularly polycythemia or myeloid metaplasia. In the most preferred embodiments, the subject has gout or Lesch-Nyhan Syndrome.

In the practice of the invention, administrating may be effected by repetitive administration of small doses of the compound over a period of time. Preferably, the administrating is by injection, or by oral, sub-lingual, transdermal or rectal means. The amount of the compound effective in the practice of the present invention is any amount which reduces the content of uric acid in the body of the subject. In embodiments where administration is accomplished by injection, or by oral, sub-lingual, transdermal or rectal means, an effective amount is an amount sufficient to achieve from 0.5 microgram/ml. to 70 microgram/ml. concentration of the compound of the blood plasma of the subject. Preferably, the effective concentration-decreasing amount of the compound is such that it will achieve from 2.5 microgram/ml. to 55 microgram/ml. concentration of the compound in the blood plasma of the subject.

Injection may be effected by intravenous, subcutaneous, intraperitoneal or intramuscular means. Intravenous injection is the preferred means and may include continous infusion of the compound.

In embodiments where the administrating is effected by injection, the effective content-decreasing amount is from 10 mg/sq.m/day to 750 mg/sq.m/day. In embodiments where administrating is effected by oral, sub-lingual, transdermal or rectal means, the effective content decreasing amount is from 20 mg/day to 4,500 mg/day.

Any barbiturate compound mono-substituted at the carbon-5 position may be used in the practice of the invention. However, since substitution of long carboxyl or poly-aromatic groups increase the central nervous system toxicity, it is a preferred that R is an alkyl group having from one to seven carbon atoms, a cycloalkyl group having one cyclo group moiety bound to an alkyl group moiety having from one carbon atom to seven carbon atoms, a hydroxyphenyl group, a heteroatomic-substituted phenyl group, a phenylalkyl group having one phenyl group moiety bound to the alkyl group moiety, a heteroatomic group having from two atoms to seven atoms, or an aryl group having one phenyl group moiety and a heteroatomic group moeity having from two atoms to seven atoms.

The barbiturate compounds suitable in the practice of this invention include barbiturate compounds where X is a hydrogen atom, oxybarbiturate compounds where X is an oxygen atom and thiobarbiturate compounds where X is a sulfur atom. Preferably, the barbiturate compounds are mono-substituted at the carbon-5 position with a methyl, ethyl, propyl, isopropyl, butyl, sec-butyl, isobutyl, pentyl, isopentyl, 2-cyclopenten-1-yl, hexyl, cyclohexen-1-yl, 1-cyclohexene-1-yl, heptyl, heptenyl, cyclohepten-1-yl, 2-bromoalkyl, 2-methylthioethyl, 1-methylbutyl, 1-methyl-2-pentynyl, 1-methyl-1-butenyl, phenyl, phenylalkyl, N-phenylcarboximido, N-methyl-carboximido, N-ethyl-carboximido, N-propyl-carboximido, N-isopropyl-carboximido, N-butyl-carboximido, N-tertbutyl-carboximido, N-pentyl-carboxmido, N-isopentyl-carboximido, N-cyclohexenyl-carboiximido, N-cyclopentenyl-carboximido, N-methyl-butyl-carboximido, N-cycloheptenyl-carboximido, N-(2-bromoallyl)-carboximido, N-(n-hexyl)-carboximido, N-(1-methyl-2-pentynyl)-carboximido or N-(1-methyl-1-butenyl)-carboximido group.

In the most preferred embodiments, the barbiturate compound is an oxy- or thiobarbiturate compound and is 5-(N-phenylcarboximido)-2-oxybarbituric acid, 5-(N-phenylcarboximido)-2-des-oxy-barbituric acid, 5-(N-phenylcarboximido)-2-oxy-4'-hydroxy-barbituric acid, 5-(N-phenylcarboximido)-2-thio-barbituric acid, 5-(N-phenylcarboximido)-2-des-thio-barbituric acid or 5-(N-phenylcarboximido)-2-thio-4'-hydroxy-barbituric acid.

The type of chain linkage of the substituted groups to the C-5 position of the barbiturate ring is not an essential feature for the effect of these compounds on uric acid metabolism. The clinical linkages may consist of (but are not limited to) keto, hydroxyl, amido, imido, carboxamido, carboximido, sulfonyl, oxo, ether, or ester. Similarly, substitution at the $R_1$ position may be undertaken to increase the pharmaceutical acceptability of the compound.

The invention also provides a method for treating a disorder of uric acid metabolism in a subject which comprises administrating to the subject a compound having the structure:

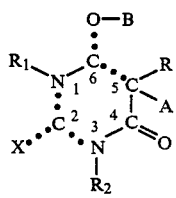

wherein X, R, $R_1$, $R_2$, A, B, and the dotted lines are the same as previously defined.

In addition, the present invention provides a method of treating a subject with an ailment caused by an abnormally high bodily content of uric acid in the subject. Treatable ailments include arthritis, kidney stones, kidney failure, urolithiasis, plumbism, hyperparathyroidism, psoriasis, sarcoidosis or cardiovascular disease. The invention is particularly useful for the treatment of arthritis, kidney failure or urolithiasis.

Another aspect of the invention concerns a pharmaceutical composition for treating disorders of uric acid metabolism in a subject which comprises a pharmaceutically acceptable carrier and an effective amount of a compound having the structure:

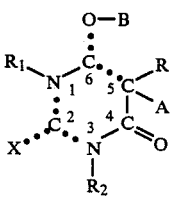

wherein X, R, $R_1$, $R_2$, A, B, and the dotted lines are the same as previously defined.

Preferred carriers include N-methyl glucamine or saline and the preferred barbiturate compound is mono-substituted at the carbon-5 position with a methyl, ethyl, propyl, isopropyl, butyl, sec-butyl, isobutyl, pentyl, isopentyl, 2-cyclopenten-1-yl, hexyl, cyclohexen-1-yl, 1-cyclohexene-1-yl, heptyl, heptenyl, cyclohepten-1-yl, 2-bromoalkyl, 2-methylthioethyl, 1-methylbutyl, 1-methyl-2-pentynyl, 1-methyl-1-butenyl, phenyl, phenylalkyl, N-phenylcarboximido, N-methylcarboximido, N-ethyl-carboximido, N-propylcarboximido, N-isopropyl-carboximido, N-butylcarboximido, N-terbutyl-carboximido, N-pentylcarboxmido, N-isopentyl-carboximido, N-cyclohexenylcarboximido, N-cyclopentenyl-carboximido, N-methyl butyl-carboximido, N-cycloheptenyl-carboximido, N-(2-bromoallyl)-carboximido, N-(n-hexyl)-carboximido, N-(1-methyl-2-pentynyl)-carboximido or N-(1-methyl-1-butenyl)-carboximido group. In the most preferred embodiments the pharmaceutical composition comprises a 5-(N-phenylcarboximido)-2-oxybarbituric acid, 5-(N-phenyl carboximido)-2-des-oxy-barbituric acid, 5-(N-phenyl carboximido)-2-oxy-4'-hydroxy-barbituric acid, 5-(N-phenylcarboximido)-2-thio-barbituric acid, 5-(N-phenylcarboximido)-2-des-thio-barbituric acid or 5-(N-phenylcarboximido)-2-thio-4'-hydroxy-barbituric acid.

Certain embodiments of this invention are exemplified in the Experimental Detail section which follows. The Experimental Detail section is set forth to aid in the understanding of the invention but is not intended to, and should not be construed to, limit in any way the invention as set forth in the claims which follows thereafter.

EXPERIMENTAL DETAIL

Various C-5 mono- and di-substituted barbiturates have been synthesized in the past for both hypnotic (i.e. sleep-inducing) and anticancer uses. Observations have shown that administration of a C-5 mono-substituted barbiturate to human subjects unexpectedly caused a dramatic decrease in serum uric acid. There is no teaching in the literature regarding similar reactions having been caused by these drugs.

Clinical and pharmacologic studies have been conducted by the inventor. In the first clinical study, a preparation of 5-(N-phenylcarboximido)-2-thiobarbituric acid was used. The drug was administered by continous intravenous infusion daily for 5 consecutive days to 19 human subjects. The daily dose ranged from 100–750 mg/sq.m/day. A decrease in serum concentration of uric acid occurred promptly in all patients. Examples of the change in serum uric acid are shown in Table 1. Of note is that the change occurred promptly and was reversible.

TABLE 1

Change in Serum Uric Acid Concentration Before, During, and After Treatment with 5-(N—phenylcarboximido)-2-thiobarbituric acid Administered Daily for 5 Days (Days 1–5)

| Subject | Dose (mg/squ.m) | Serum Uric Acid Concentration (mg/dl) | | | | |
|---|---|---|---|---|---|---|
| | | Initial | Lowest | (day) | Recovery | (day) |
| 1 | 100 | 4.2 | 0.8 | (7) | 4.8 | (10) |
| 1a | 100 | 4.8 | 1.2 | (4) | 5.6 | (10) |
| 2 | 100 | 6.2 | 1.1 | (5) | 5.3 | (17) |
| 3 | 100 | 6.9 | 1.8 | (6) | 5.8 | (8) |
| 3a | 100 | 6.6 | 1.0 | (6) | 5.1 | (20) |
| 4 | 150 | 6.2 | 2.0 | (6) | 4.4 | (7) |
| 5 | 150 | 6.2 | 1.9 | (3) | 4.6 | (12) |
| 6 | 150 | 3.4 | 1.0 | (3) | 3.5 | (11) |
| 7 | 200 | 5.7 | 0.8 | (7) | 4.2 | (12) |
| 8 | 200 | 3.7 | 0.7 | (3) | 2.6 | (10) |
| 9 | 250 | 5.8 | 1.2 | (6) | 6.2 | (10) |
| 10 | 250 | 4.4 | 0.8 | (5) | 4.0 | (11) |
| 11 | 250 | 7.8 | 1.3 | (5) | 5.9 | (8) |
| 12 | 300 | 5.0 | 2.4 | (3) | 5.5 | (10) |
| 13 | 300 | 5.0 | 0.8 | (3) | 4.0 | (11) |
| 14 | 300 | 9.9 | 1.7 | (5) | 7.4 | (10) |
| 15 | 400 | 4.4 | 1.0 | (5) | 3.0 | (6) |
| 16 | 400 | 5.1 | 1.9 | (8) | 4.0 | (10) |
| 17 | 500 | 5.2 | 1.2 | (5) | 3.3 | (8) |
| 18 | 500 | 4.9 | 1.3 | (5) | 3.8 | (11) |
| 19 | 750 | 9.0 | 1.4 | (5) | 4.7 | (15) |

Of importance, the effects upon uric acid metabolism occurred at the lowest dose tested (i.e. 100 mg/sq. m/day) and the effect was reversible upon discontinuation of the drug. Similarly important is the observation that patients who were re-treated with the compound showed a repeated decline in serum uric acid (Subjects 1 and 1a, 3 and 3a: Table 1). The rapid onset of action, freedom from toxicity (especially central nervous system reactions), lack of resistance to the effect upon re-treatment, and reversible nature of the pharmacologic effect are all extremely desirable features of this invention.

As part of the laboratory investigation, the possiblity that C-5-mono-substituted barbiturates might interfere with the measurement of uric acid in blood was considered, since such interference produces spuriously high or low values. Approximately 20 ml of whole blood was taked from a volunteer donor and divided into equal aliquots. A solution of 5-(N-phenylcarboximido)-2-thiobarbituric acid was prepared using serial dilutions of sterile normal saline. An amount of drug solution was added to test tubes to achieve final concentrations of approximately 10, 30, and 50 microgram/ml in whole blood. Said concentrations are pharmacologically achieved in human subjects without toxicity (Haines, I. et al., Proc. Am. Assoc. Cancer Res. 28: 192, 1987). The blood samples were then coded and sent to a clinical biochemistry lab for blinded determination of uric acid via an autoanalyzer (Technicon Inc., Tarrytown, NY) which employed an enzymatic method (i.e. uricase). Serum was separated from whole blood via centrifugation. As shown in Table 2, the addition of 5-(N-phenylcarboximido)-2-thiobarbituric acid to whole blood over a range of concentrations did not significantly alter the detection of uric acid in serum. Thus, the occurrence of low uric acid after treatment of human subjects with a C-5-mono-substituted barbiturate was not due to laboratory artifact.

TABLE 2

Lack of Alteration in Measured Serum Uric Acid Concentration After Addition of 5-(N—phenylcarboximido)-2-thiobarbituric Acid

| Test Code# (mg/dl) | Approximate Drug Concentration (g/ml) | Uric Acid Concentration |
|---|---|---|
| TB87620 | 10 | 4.8 |
| MF87418 | 30 | 4.7 |
| RW45439 | 50 | 4.6 |

What is claimed is:

1. A method for decreasing an abnormally high bodily content of uric acid in a subject in need thereof which comprises administrating to the subject an effective content-decreasing amount of a compound having the structure:

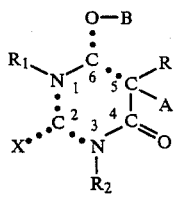

wherein:
X is an oxygen, sulfur or hydrogen atom;
R is an alkyl, a cycloalkyl, a phenyl, a phenylalkyl, a hydroxyphenyl, an amino, a hydroxyl, an aryl comprising an aromatic ring or cyclo moiety bound to an alkyl, N-phenylcarboximido, N-methyl-carboximido, N-ethyl-carboximido, N-propyl-carboximido, N-isopropyl-carboximido, N-butyl-carboximido, N-terbutyl-carboximido, N-pentyl-carboximido, N-isopentyl-carboximido, N-cyclohexenyl-carboximido, N-cyclopentenyl-carboximido, N-methylbutyl-carboximido, N-cycloheptenyl-carboximido, N-(2-bromoallyl)-carboximido, N-(n-hexyl)-carboximido, N-(1-methyl-2-pentynyl)-carboximido or N-(1-methyl-1-butenyl)-carboximido;
$R_1$ may be present or absent and if present is a hydrogen atom or a methyl group;
$R_2$ may be present or absent and if present is a hydrogen atom or a methyl group;

either A or B is present and the other is absent and if present is a hydrogen atom; and
the dotted lines ( . . . ) represent bonds which may be double or single bonds;
and wherein:
the dotted line ( . . . ) between C-6 and O is a double bond if A is present and a single bond if B is present;
the dotted line ( . . . ) between C-6 and C-5 is a double bond if B is present and a single bond if A is present;
the dotted line ( . . . ) between C-2 and X is a double bond and both $R_1$ and $R_2$ are present if X is an oxygen or sulfur atom;
the dotted line ( . . . ) between C-2 and X is a single bond and either $R_1$ or $R_2$ is present and the other is absent if X is a hydrogen atom;
the dotted line ( . . . ) between N-1 and C-2 is a single bond if $R_1$ is present and a double bond if $R_1$ is absent; and
the dotted line ( . . . ) between N-3 and C-2 is a single bond if $R_2$ is present and a double bond if $R_2$ is absent.

2. A method of claim 1, wherein the subject is a human or an animal.

3. A method of claim 2, wherein the subject has a disorder or uric acid metabolism characterized by an abnormally high content of uric acid in the body of the subject.

4. A method of claim 3, wherein the disorder is an overproduction of uric acid, a low excretion of uric acid, tumor lysis, or a blood disorder.

5. A method of claim 4, wherein the blood disorder is polycythemia or myeloid metaplasia.

6. A method of claim 3, wherein the disorder is gout.

7. A method of claim 3, wherein the disorder is Lesch-Nyhan Syndrome.

8. A method of claim 1, wherein the administrating is effected by injection, or by oral, sub-lingual, transdermal or rectal means.

9. A method of claim 8, wherein the administrating is effected by repetitive administration of small but effective doses of the compound over a period of time.

10. A method of claim 8, wherein the effective content-decreasing amount is sufficient to achieve from 0.5 microgram/ml. to 70 microgram/ml. concentration of the compound in the blood plasma of the subject.

11. A method of claim 10, wherein the effective content-decreasing amount is sufficient to achieve from 2.5 microgram/ml. to 55 microgram/ml. concentration of the compound in the blood plasma of the subject.

12. A method of claim 8, wherein the injection is intravenous, subcutaneous, intraperitoneal, or intramuscular.

13. A method of claim 12, wherein the intravenous injection is continuous infusion.

14. A method of claim 12, wherein the effective content-decreasing amount is from 10 mg/sq.m/day to 750 mg/sq.m/day.

15. A method of claim 8, wherein the administrating is effected by oral, sub-lingual, transdermal or rectal means.

16. A method of claim 15 wherein the effective content-decreasing amount is from 20 mg/day to 4,500 mg/day.

17. A method of claim 1, wherein R is an alkyl having from one carbon atom to seven carbon atoms; a cycloalkyl having one cyclo moiety bound to an alkyl moiety having from one carbon atom to seven carbon atoms; a hydroxyphenyl, a phenylalkyl having one phenyl moiety bound to the alkyl moiety; or an aryl having one phenyl moiety.

18. A method of claim 17, wherein the compound is a thiobarbiturate.

19. A method of claim 18, wherein the thiobarbiturate is 5-(N-phenylcarboximido)-2-thio-barbituric acid, 5-(N-phenylcarboximido)-2-des-thio-barbituric acid or 5-(N-phenylcarboximido)-2-thio-4'-hydroxy-barbituric acid.

20. A method of claim 17, wherein the compound is an oxybarbiturate.

21. A method of claim 20, wherein the oxybarbiturate is mono-substituted at the carbon-5 position with a methyl, ethyl, propyl, isopropyl, butyl, sec-butyl, isobutyl, pentyl, isopentyl, 2-cyclopenten-1-yl, hexyl, cyclohexen-1-yl, 1-cyclohexene-1-yl, heptyl, heptenyl, cyclohepten-1-yl, 2-bromoalkyl, 2-methylthioethyl, 1-methylbutyl, 1-methyl-2-pentynyl, 1-methyl-1-butenyl, phenyl, phenylalkyl, N-phenylcarboximido, N-methyl-carboximido, N-ethyl-carboximido, N-propyl-carboximido, N-isopropyl-carboximido, N-butyl-carboximido, N-terbutyl-carboximido, N-pentyl-carboximido, N-isopentyl-carboximido, N-cyclohexenyl-carboximido, N-cyclopentenyl-carboximido, N-methylbutyl-carboximido, N-cycloheptenyl-carboximido, N-(2-bromoallyl)-carboximido, N-(n-hexyl)-carboximido, N-(1-methyl-2-pentynyl)-carboximido or N-(1-methyl-1-butenyl)-carboximido group.

22. A method of claim 21, wherein the oxybarbiturate is 5-(N-phenylcarboximido)-2-oxy-barbituric acid, 5-(N-phenylcarboximido)-2-des-oxy-barbituric acid or 5-(N-phenylcarboximido)-2-oxy-4'-hydroxy-barbituric acid.

23. A method of treating a subject having a disorder of the uric acid metabolism characterized by an abnormally high bodily content of uric acid in the blood serum, urine or joints of the subject which comprises administrating to the subject a compound having the structure:

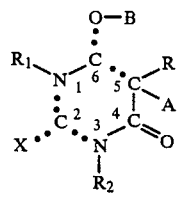

wherein:
X is an oxygen, sulfur or hydrogen atom;

R is an alkyl, a cycloalkyl, a phenyl, a phenylalkyl a hydroxyphenyl, an amino, a hydroxyl, or an aryl comprising an aromatic ring, cyclo moiety bound to an alkyl, N-phenylcarboximido, N-methyl-carboximido, N-ethyl-carboximido, N-propyl-carboximido, N-isopropyl-carboximido, N-butyl-carboximido, N-terbutyl-carboximido, N-pentyl-carboximido, N-isopentyl-carboximido, N-cyclohexenyl-carboximido, N-cyclopentenyl-carboximido, N-methylbutyl-carboximido, N-cycloheptenyl-carboximido, N-(2-bromoallyl)-carboximido, N-(n-hexyl)-carboximido, N-(1-methyl-2-pentyntl)-carboximido or N-(1-methyl-1-butenyl)carboximido;

$R_1$ may be present or absent and if present is a hydrogen atom or a methyl group;

$R_2$ may be present or absent and if present is a hydrogen atom or a methyl group;

either A or B is present and the other is absent and if present is a hydrogen atom; and the dotted lines ( . . . ) represent bonds which may be double or single bonds;

and wherein:

the dotted line ( . . . ) between C-6 and O is a double bond if A is present and a single bond if B is present;

the dotted line ( . . . ) between C-6 and C-5 is a double bond if B is present and a single bond if A is present;

the dotted line ( . . . ) between C-2 and X is a double bond and both $R_1$ and $R_2$ are present if X is an oxygen or sulfur atom;

the dotted line ( . . . ) between C-2 and X is a single bond and either $R_1$ or $R_2$ is present and the other is absent if X is a hydrogen atom;

the dotted line ( . . . ) between N-1 and C-2 is a single bond if $R_1$ is present and a double bond if $R_1$ is absent; and the dotted line ( . . . ) between N-3 and C-2 is a single bond if $R_2$ is present and a double bond if $R_2$ is absent.

24. A method of treating a subject with a disorder of uric acid metabolism characterized by an abnormally high bodily content of uric acid in the blood serum, urine or joints of the subject which comprises decreasing the content of uric acid in the subject by the method of claim 1.

25. A method of claim 24, wherein the disorder is arthritis, kidney stones, kidney failure, urolithiasis, a cardiovascular disease, plumbism, hyperparathyroidism, psoriasis, or sarcoidosis.

26. A method of claim 25, wherein the disorder is arthritis, kidney failure or urolithiasis.

* * * * *